US007972270B2

United States Patent
Hamada

(10) Patent No.: US 7,972,270 B2
(45) Date of Patent: Jul. 5, 2011

(54) ULTRASOUND IMAGING APPARATUS AND METHOD HAVING TWO DIMENSIONAL FOCUS

(75) Inventor: Kenji Hamada, Tochigi (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 493 days.

(21) Appl. No.: 11/125,174

(22) Filed: May 10, 2005

(65) Prior Publication Data
US 2005/0256407 A1 Nov. 17, 2005

(30) Foreign Application Priority Data

May 11, 2004 (JP) ................................. 2004-141432

(51) Int. Cl.
*A61B 8/00* (2006.01)
(52) U.S. Cl. ........................................................ 600/447
(58) Field of Classification Search .......... 600/437–447, 600/463
See application file for complete search history.

(56) References Cited

U.S. PATENT DOCUMENTS

| 5,381,693 | A | * | 1/1995 | Kobayashi et al. | ............. 73/614 |
| 6,310,831 | B1 | * | 10/2001 | Dillman | ........................ 367/105 |
| 6,374,674 | B1 | * | 4/2002 | Mine | ............................... 73/606 |
| 2003/0023166 | A1 | * | 1/2003 | Frisa et al. | ..................... 600/443 |

FOREIGN PATENT DOCUMENTS

| JP | 62-25375 | 6/1987 |
| JP | 3-73136 | 3/1991 |

* cited by examiner

*Primary Examiner* — Eric F Winakur
*Assistant Examiner* — Michael T Rozanski
(74) *Attorney, Agent, or Firm* — Oblon, Spivak, McClelland, Maier & Neustadt, L.L.P.

(57) ABSTRACT

An ultrasound imaging apparatus includes an ultrasonic probe configured to transmit an ultrasonic beam to an object and receive a reflective ultrasonic signal, a controller configured to control the ultrasonic probe such that the ultrasonic beam is focused on focus positions in at least two directions, each of which is substantially perpendicular to a transmission and reception direction, an image generation unit configured to generate an ultrasonic image based on the reflective ultrasonic signal and a display unit configured to display the at least two focus positions or the focus position in the direction which is substantially perpendicular to the ultrasonic image with the ultrasonic image.

11 Claims, 9 Drawing Sheets

ULTRASOUND IMAGING APPARATUS AND METHOD HAVING TWO DIMENSIONAL FOCUS

CROSS-REFERENCE TO RELATED APPLICATIONS

This application is based upon and claims the benefit of priority from prior Japanese Patent Application No. P2004-141432 filed on May 11, 2004, the entire contents of which are incorporated herein by reference.

FIELD OF THE INVENTION

The present invention is related to an ultrasound imaging apparatus and method of ultrasound imaging, and especially the apparatus and the method that displays a focus position.

BACKGROUND

An ultrasound imaging apparatus transmits an ultrasonic beam generated from an ultrasonic transducer in an ultrasonic probe to a patient, receives an ultrasonic reflective wave produced according to difference in sound impedance of a tissue of the patient with the ultrasonic transducer, and displays an ultrasonic image on a monitor. Since a 2-dimensional image can be observed easily in real time by easy operation, such as contacting the ultrasonic probe to a body surface, the ultrasound imaging method is widely used for functional diagnosis or morphological diagnosis of various internal organs of the patient.

As an example of a scan method of the ultrasonic imaging apparatus, there is an electronic scan method. In the electronic scan method, timing of transmission of the ultrasonic wave and timing of generation of received signals of ultrasonic transducers that are arranged at a tip of the ultrasonic probe are controlled by electronic switches and delay circuits, in order that an direction of the ultrasonic beam according to an arranging direction and a focus position are freely changed.

From the focus position where the ultrasonic beam is most focused, relatively stronger reflective wave of the ultrasonic beam can be obtained than that from other positions. In other words, a high resolution image is obtained near the focus position, and a low resolution image is obtained on other positions far from the focus position.

Predetermined amount of delay is given by each delay circuit connected to each ultrasonic transducer so that the focus position corresponds to a region to be observed in the patient.

However, it is difficult to recognize the focus position only from the image of the ultrasonic wave. In order to showing where the focus position located in the image, the ultrasound imaging apparatus, such as disclosed in Japanese Patent (Kokoku) No. 62-25375, is known. The ultrasound imaging apparatus includes a beam character recognition part that recognizes the focus position of the ultrasonic beam and a display part that displays the focus position recognized by the beam character recognition part. According to the ultrasound imaging apparatus, it is possible to recognize which portion is the highest or relatively higher resolution in the displayed ultrasonic image obtained by the transmission and reception of the ultrasonic wave.

By the way, in various cases, homogeneity of intensity of the ultrasonic wave in a transmission and reception direction of an ultrasonic beam or homogeneity of resolution is important. For example, in a technique called Contrast Echo method, a harmonic signal generated by destruction of small air bubbles injected into the patient according to a high power ultrasonic wave is measured. Unless the high power ultrasonic wave is uniform, destruction of the bubbles is not performed homogeneously, and a blood vessel to be observed cannot be recognized correctly.

In Color Flow Mapping (CFM) method, information of flow velocity, such as blood flow velocity, obtained by Doppler method, is superimposed on the ultrasonic image that shows a shape. Also in this method, the homogeneity of quality of image is required since comparison of the blood vessels to be observed is performed in a wide range.

Furthermore, when a biopsy needle is inserted into the patient, the ultrasound imaging apparatus is used for checking a location of the inserted needle. In this case, it is desirable that a wide range from a surface of the patient to a portion which the biopsy needle is injected to is displayed homogeneously in order that an insertion path can be easily recognized.

Thus, in various methods, homogeneity of intensity of the ultrasonic wave or whole homogeneity of resolution of image is more important than local high resolution of image. Therefore, when using the above mentioned conventional methods, it is generally known that defocusing ultrasonic beam is used or the ultrasonic beam is repeatedly transmitted or received several times during changing the focus position, called as multi focus method, to improve the homogeneity of the image by homogenizing the resolution of the image.

Also in this case, the technology disclosed in Japanese Patent (Kokoku) No. 62-25375 is useful. By referring displayed beam characteristics and adjusting the focus position, a desired quality of image can be obtained.

By the way, in a 2-dimensional array probe proposed in recent years, ultrasonic transducers arranged in 2-directions, and delay control can be performed in the 2-directions. For example, when the homogeneity of the image should be important as mentioned above, the focus position is controlled in the 2-directions independently, two focus positions are located in different locations between region of interest. Thereby, the region of interest is displayed homogeneously.

A method where the beam focus positions can be located in different locations in 2-directions is useful, especially when the homogeneity of the image is improved by beam defocusing method or the multi-focus method, since the both methods have problems, such as deterioration of image or frame rate.

However, in the conventional technology as disclosed in Japanese Patent (Kokoku) No. 62-25375, an ultrasonic scan is performed only one direction along an arrangement of ultrasonic transducers, and a single focus position is displayed in the direction.

In other words, Japanese Patent (Kokoku) No. 62-25375 does not disclose the focus positions of the 2-dimensional array probe are controlled and displayed in 2-dimension.

Even if the 2-dimensional array probe is adopted to the conventional technique as disclosed in Japanese Patent (Kokoku) No. 62-25375, it is difficult to recognize and set the focus positions in 2-dimension is consideration for relationship of the focus positions.

SUMMARY

One object of the present invention is to ameliorate the above-mentioned problems and to provide an ultrasound imaging apparatus or method by which focus positions in predetermined directions can be easily recognized.

According to one aspect of the present invention, there is provided an ultrasound imaging apparatus comprises an ultrasonic probe configured to transmit an ultrasonic beam to an object and receive a reflective ultrasonic signal, a controller configured to control the ultrasonic probe such that the ultrasonic beam is focussed on focus positions in at least two directions, each of which is substantially perpendicular to a transmission and reception direction, an image generation unit configured to generate an ultrasonic image based on the reflective ultrasonic signal, and a display unit configured to display the at least two focus positions in the at least two directions with the ultrasonic image.

According to another aspect of the present invention, there is provided an ultrasound imaging apparatus comprises an ultrasonic probe configured to transmit an ultrasonic beam to an object and receive a reflective ultrasonic signal, a controller configured to control the ultrasonic probe such that the ultrasonic beam is focussed on focus positions in at least two directions, each of which is substantially perpendicular to a transmission and reception direction, an image generation unit configured to generate an ultrasonic image based on the reflective ultrasonic signal, and a display unit configured to display the focus position in the direction which is substantially perpendicular to the ultrasonic image with the ultrasonic image.

According to another aspect of the present invention, there is provided a method of ultrasound imaging comprises transmitting an ultrasonic beam to an object and receiving a reflective ultrasonic signal, controlling the ultrasonic probe such that the ultrasonic beam is focussed on focus positions in at least two directions, each of which is substantially perpendicular to a transmission and reception direction, generating an ultrasonic image based on the reflective ultrasonic signal, and displaying the at least two focus positions in the at least two directions with the ultrasonic image.

According to another aspect of the present invention, there is provided a method of ultrasound imaging comprises transmitting an ultrasonic beam to an object and receiving a reflective ultrasonic signal, controlling the ultrasonic probe such that the ultrasonic beam is focussed on focus positions in at least two directions, each of which is substantially perpendicular to a transmission and reception direction, generating an ultrasonic image based on the reflective ultrasonic signal, and displaying the focus position in the direction which is substantially perpendicular to the ultrasonic image with the ultrasonic image.

BRIEF DESCRIPTION OF THE DRAWINGS

A more complete appreciation of the invention and many of the attendant advantages thereof will be readily obtained as the same becomes better understood by reference to the detailed description when considered in connection with the accompanying drawings. In the drawings.

DETAILED DESCRIPTION OF EXEMPLARY EMBODIMENTS

Figure 1:
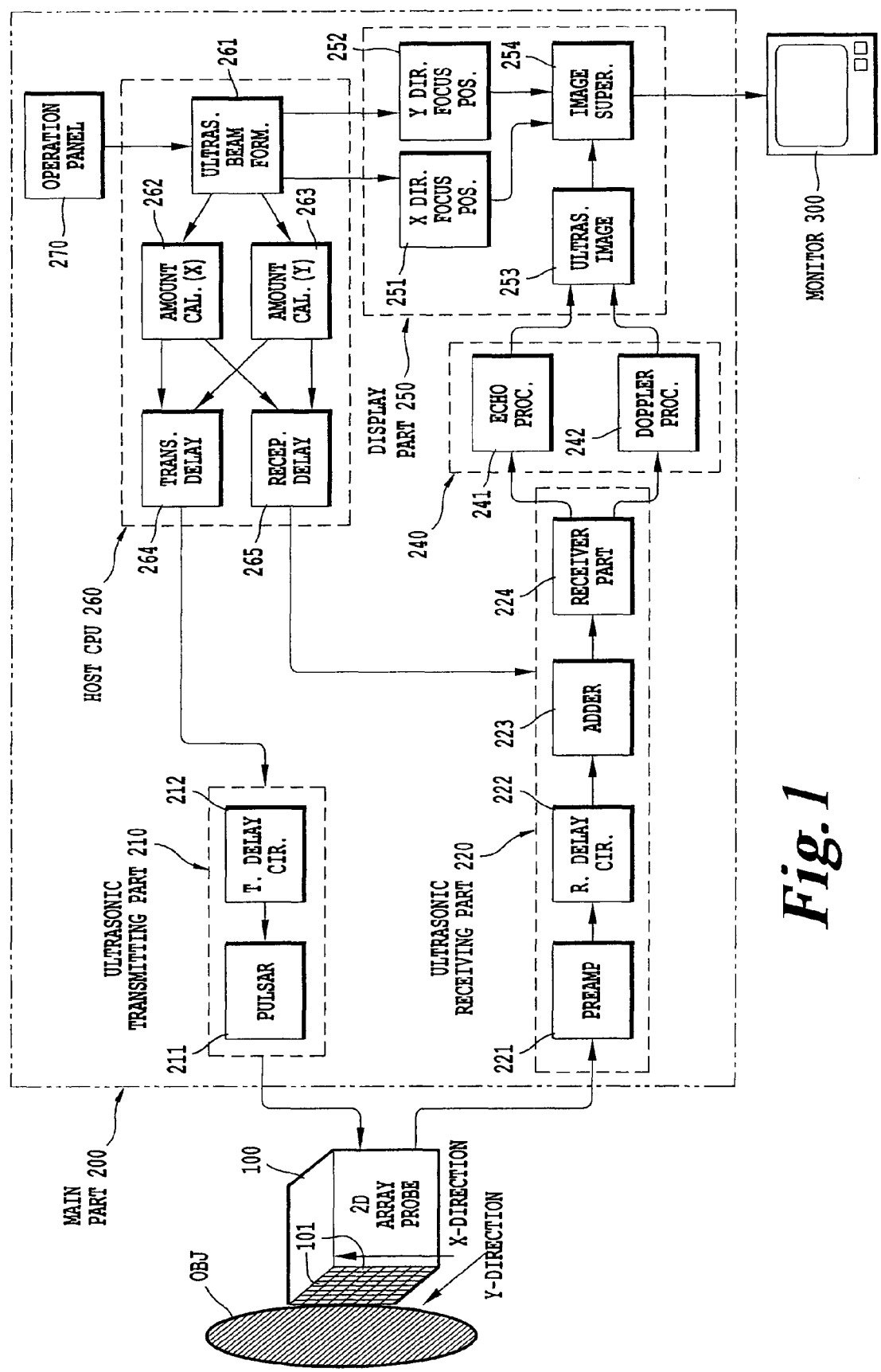
FIG. 1 is a block diagram of an ultrasound imaging apparatus.

Hereafter, an embodiment of an ultrasound apparatus is explained with reference to a drawing. The ultrasound imaging apparatus shown in FIG. 1 scans an ultrasonic beam in 2-dimension to obtain 3-dimensional image and includes a 2-dimensional array probe 100 by which 2-dimensional scan can be performed, a main part 200 to which the 2-dimensional array probe 100 is connected, and a monitor 300 connected to the main part 200.

In the 2-dimensional array probe 100, a plurality of ultrasonic transducers 101 are arranged in 2-dimension in X and Y directions. Each ultrasonic transducer is driven under control of the main part 200, and according to a predetermined ultrasonic beam form, the ultrasonic beam is transmitted to a diagnostic part in a patient OBJ.

The 2-dimensional array probe receives an ultrasonic echo signal which reflects on sound impedance boundary in the patient or is scattered by a small clutter, changes the ultrasonic echo signal into an electric echo signal of voltage, and sends the electric echo signal the main part 200.

The main part 200 is connected to the 2-dimensional array probe 100 and includes an ultrasonic transmitting part 210, an ultrasonic receiving part 220, an image-processing part 240 connected to output side of the ultrasonic receiving part 220, a display processing part 250 connected to the image-processing part 240, an operation panel 270 and a host CPU 260 connected to the parts.

The ultrasonic transmitting part 210 includes a pulsar 211 and a transmitting delay circuit 212. When pulses to which delay is given by the transmitting delay circuit 212 is generated in the pulsar 211 and drives the 2-dimensional array probe 100 drive, a pulse-shaped ultrasonic wave is transmitted to the region of interest in the patient OBJ. The focus position the ultrasonic wave transmitted from the 2-dimensional array probe 100 is controlled by delay processing of the transmitting delay circuit 212.

In this embodiment, since the 2-dimensional array probe is used, the control of the focus position can be performed in X and Y directions by the delay processing in the X and Y directions along arrangement of the ultrasonic transducers 101.

The ultrasonic receiving part 220 includes a preamplifier 221, a reception delay circuit 222, an adder 223 and a receiver part 224. The received signal that is outputted from each channel of the 2-dimensional array probe 100 is amplified by the preamplifier 221 and A/D converted. Delay time required to determine reception direction is given to an output signal from the preamplifier 221 in the reception delay circuit 222. An output signal from the reception delay circuit 222 is added in the adder 223. The received signal from the direction along the reception direction is emphasized by the adding. The receiver part 224 includes a logarithmic amplifier and an envelope detection circuit which receive an output signal from the adder 223 and outputs a signal to the image-processing part 240.

The image-processing part 240 includes an echo processor 241 and a Doppler processor 242, and outputs a received signal from the receiver part 224 if needed. The echo processor 241 performs quadrature detection using predetermined reference frequency to a received signal from the reception delay circuit 222, generates 3-dimensional special distribution image data which shows a 3-dimensional form information (contrast image data in which information of contrast agent is also included when the contrast agent is injected) in the patient OBJ according to signal amplitude of the detection signal, and sends the image data to the display processing part 250. Moreover, by measuring time change of phase of the received signal from the reception delay circuit 5, the Doppler processor 242 generates 3-dimensional special distribution image data, such as speed, power and distribution which show blood-flow information in the patient, sends the image data to the display processing part 250.

The display processing part 250 includes an ultrasonic image generation part 253, an X direction focus position generation part 251, a Y direction focus position generation part 252 and an image superimposing part 254. The ultrasonic image generation part 253 extracts an arbitrary sectional data from 3-dimensional image data or performs mapping of the image data on a 2-dimensional plane from an arbitrary viewpoint using a predetermined 2-dimensional mapping method to generate ultrasonic image data to be sent to the image superimposing part 254.

The X direction focus position generation part 251 obtains the focus position information in the X direction along the arrangement of the ultrasonic transducers 101 from the host CPU 260, and creates image data of the focus position in the X direction of the ultrasonic beam. The image data of the X directional focus position is sent to the image superimposing part 254. The Y direction focus position generation part 252 creates image data of Y directional focus position and sends the image data to the image superimposing part 254 as well. The image superimposing part 254 superimposes the X directional focus position image data, the Y directional focus position image data and the ultrasonic image data and changes the image data into display image data according to screen line of the monitor 300.

The host CPU 260 includes an ultrasonic beam form setting part 261, an amount calculation part 262 of X direction delay, an amount calculation part 263 of Y direction delay, a transmitting delay signal generation part 264, and a reception delay signal generation part 265. Moreover, the host CPU has a function for controlling whole parts.

The ultrasonic beam form setting part 261 sets the ultrasonic beam form in ultrasonic transmission. An operation of the setting of the ultrasonic beam form in ultrasonic transmission is performed by input from the operation panel 270. Moreover, the received ultrasonic beam form is automatically set according to period between the transmission and reception of the ultrasonic wave, since the reflective ultrasonic wave is received in turn according to distance between a portion in the patient and the 2-dimensional array probe 100. The focus position can be changed in turn even by a single transmission and reception of the ultrasonic wave.

The ultrasonic beam form setting part 261 sends information showing the ultrasonic beam form to the amount calculation part 262 of X direction delay and the amount calculation part 263 of Y direction delay. Moreover, the ultrasonic beam form setting part 261 sends information which shows the focus position to the display processing part 250 based on the set ultrasonic beam form.

The amount calculation part 262 of X direction delay and the amount calculation part 263 of Y direction delay calculates amount of delay corresponding to the delay of X and Y directions based on the ultrasonic beam form set with the ultrasonic beam form setting means 261.

The calculated amount of delay corresponding to the X and Y directions is sent to the transmitting delay signal generation part 264 and the reception delay signal generation part 265. The transmitting delay signal generation part 264 and the reception delay signal generation part 265 generate the transmission delay signal and the reception delay signal to ultrasonic transducers 101 based on the amount of delay. The transmission delay signal is sent to the ultrasonic transmitting part 210 and delay processing of the ultrasonic transmission signal is performed in the transmitting delay circuit 212. The reception delay signal is sent to the ultrasonic receiving part 220 and delay processing of the ultrasonic reception signal is performed in the reception delay circuit 222.

The operation panel 270 includes an input device, such as a joystick or a trackball, for setting or changing conditions of the transmission and reception of the ultrasonic beam in addition to a switch, various buttons, a keyboard, etc. Instruction information inputted by an operator is sent to the host CPU 260 and the setting or the changing is performed in each part of the main part 200. For example, when the operator operates the operation panel 270, watching a screen of the monitor 300, the setting or the changing of the focus position of the ultrasonic beam can be performed. The setting or the changing method of the focus position is explained below.

Figure 2:
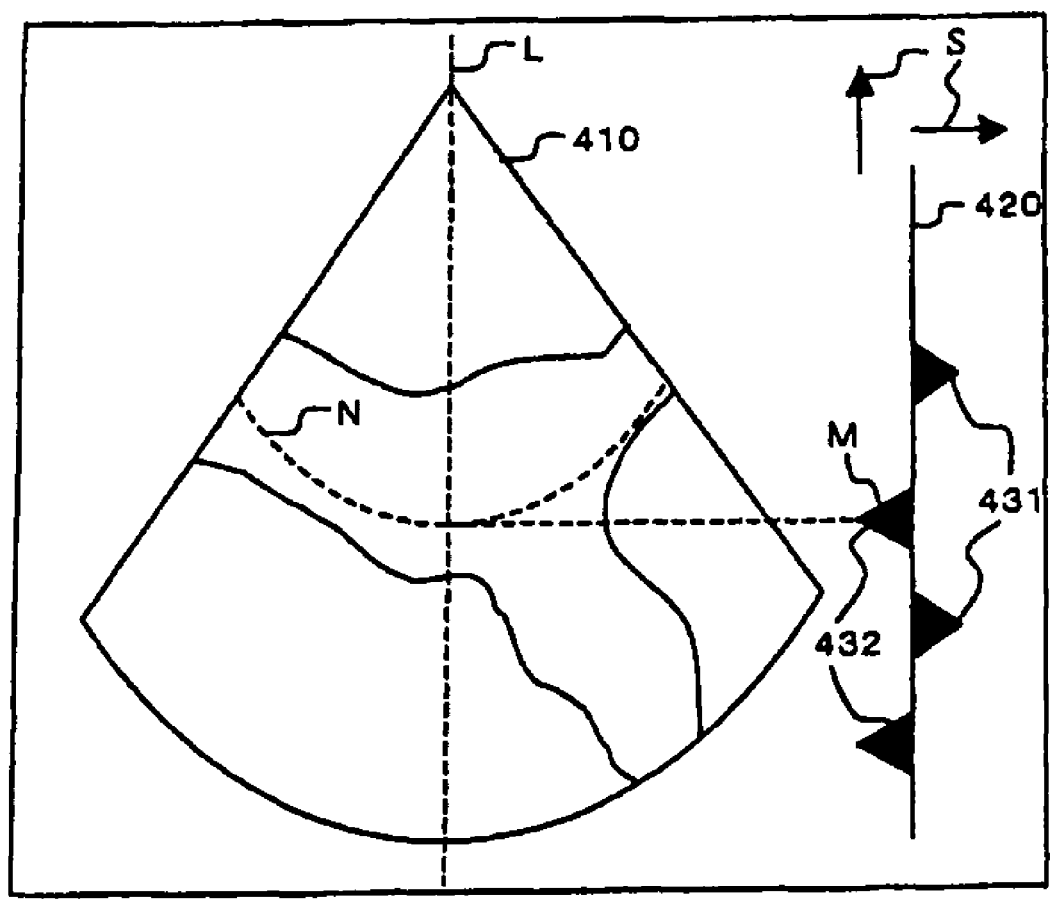
FIG. 2 is a first exemplary illustration of image displayed in a monitor.

A display of the focus position is explained referring FIG. 2 through FIG. 6. FIG. 2 shows an example of image generated in the display processing part 250. An image generated in the display processing part 250 includes 2-dimensional sectional image 410, a direction line 420 that is located beside the sectional image 410 and indicates the direction of the ultrasonic beam transmitted by the 2-dimensional array probe 100 and focal points 431 and 432 indicating the focus positions.

These focal points 431 and 432 are related to a plane near a center line L in the 2-dimensional sectional image 410 and a plane of the 2-dimensional sectional image 410 in a lateral direction, respectively. The operator recognizes where the focus positions are located in the 2-dimensional sectional image 410, observing the superimposed image including the focal points 431 and 432 and the 2-dimensional sectional image 410. For example, the operator refers the focal point M shown in FIG. 2 and recognizes that the ultrasonic beam is focused on near an arc N in the 2-dimensional sectional image 410. The line L and arc N may not be displayed.

In this embodiment, although it is explained that a sector type in which the ultrasonic scan is performed in fan shape is used by the delay control of the arranged ultrasonic transducers 101, a liner type in which the ultrasonic wave is scanned in a perpendicular direction to the arrangement direction of the ultrasonic transducers may be adopted. In that case, the focal points 431 and 432 and the 2-dimensional sectional image 410 are displayed in the lateral direction.

The focal points 431 and 432 are displayed as two kinds of features as shown in FIG. 2. Each focal point corresponds to each focus position in each different plane where the ultrasonic beam is projected. The different planes are planes A and B located along the X and Y directions. The plane A is crossed with the plane B perpendicularly on an arrow R that is along the transmission direction as shown in FIG. 3.

The 2-dimensional sectional image 410 can be located in an arbitrary section as a function included in the ultrasonic image generation part 253. In this case, relationship between the X and Y directions corresponding to the focal points 431 and 432 and the 2-dimensional sectional image is displayed. In FIG. 2, when the 2-dimensional sectional image 410 is located in parallel to the X direction, an arrow S is displayed and the relationship between the sectional plane and the planes corresponding to the focal points 431 and 432. The arrow S is displayed in the lateral direction, and the operator easily recognizes that the focal point 431 corresponds to the plane parallel to the 2-dimensional sectional image.

Figure 3:
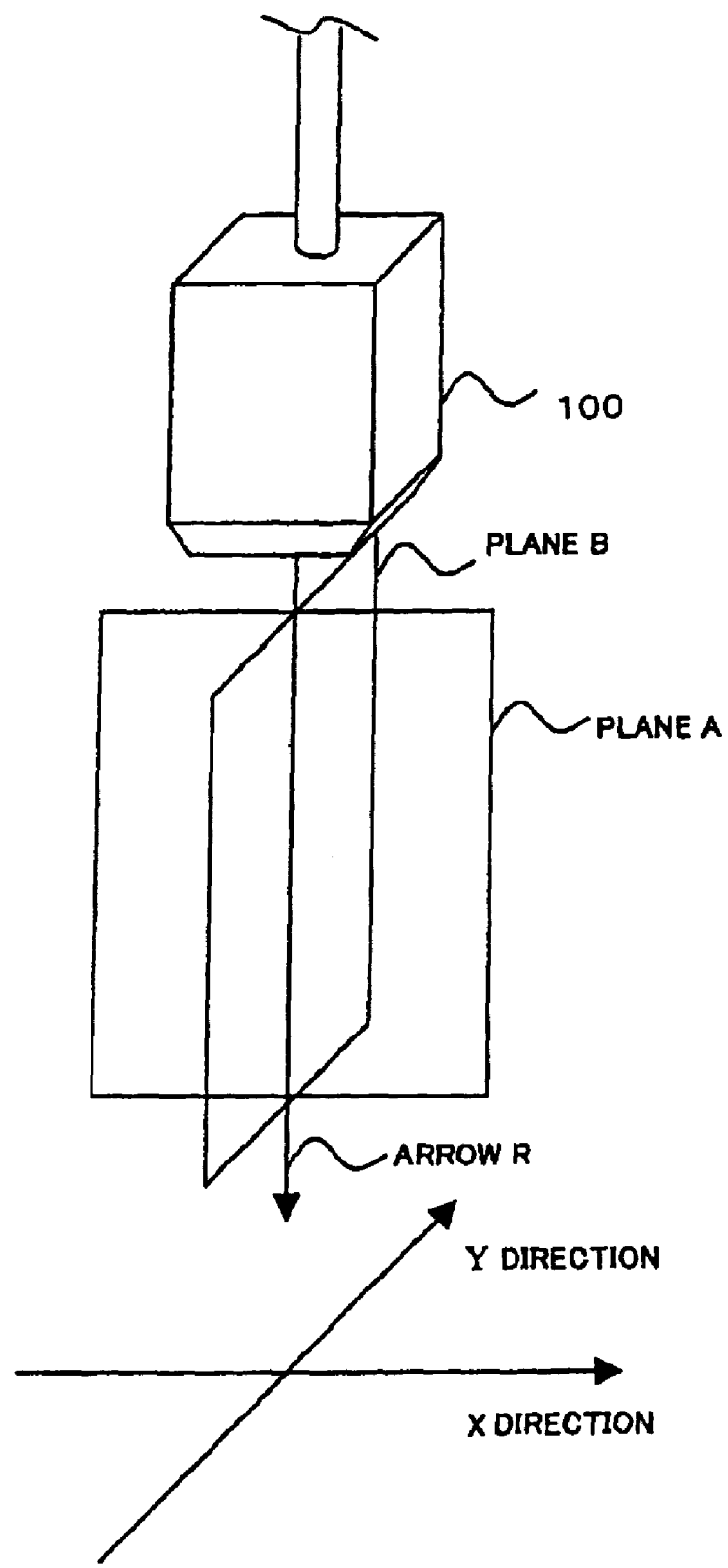
FIG. 3 is an illustration for explaining relationship between a focus position and an ultrasonic beam form.

In this case of FIG. 2, the focal point 431 is a focal point obtained based on a cross region of the plane A shown in FIG. 3 and the transmitted ultrasonic beam. The focal point 432 is a focal point obtained based on a cross region of the plane B and the transmitted ultrasonic beam.

When the multi-focus method in which the transmission and reception of the ultrasonic wave is performed several times while the focus position is changed is used, the focal points 431 and 432 whose number corresponds to the number of transmission and reception are displayed. For example, when performing ultrasonic wave transmission to the same direction twice, two focal points 431 and two focal points 432 are created, respectively.

Figure 4:
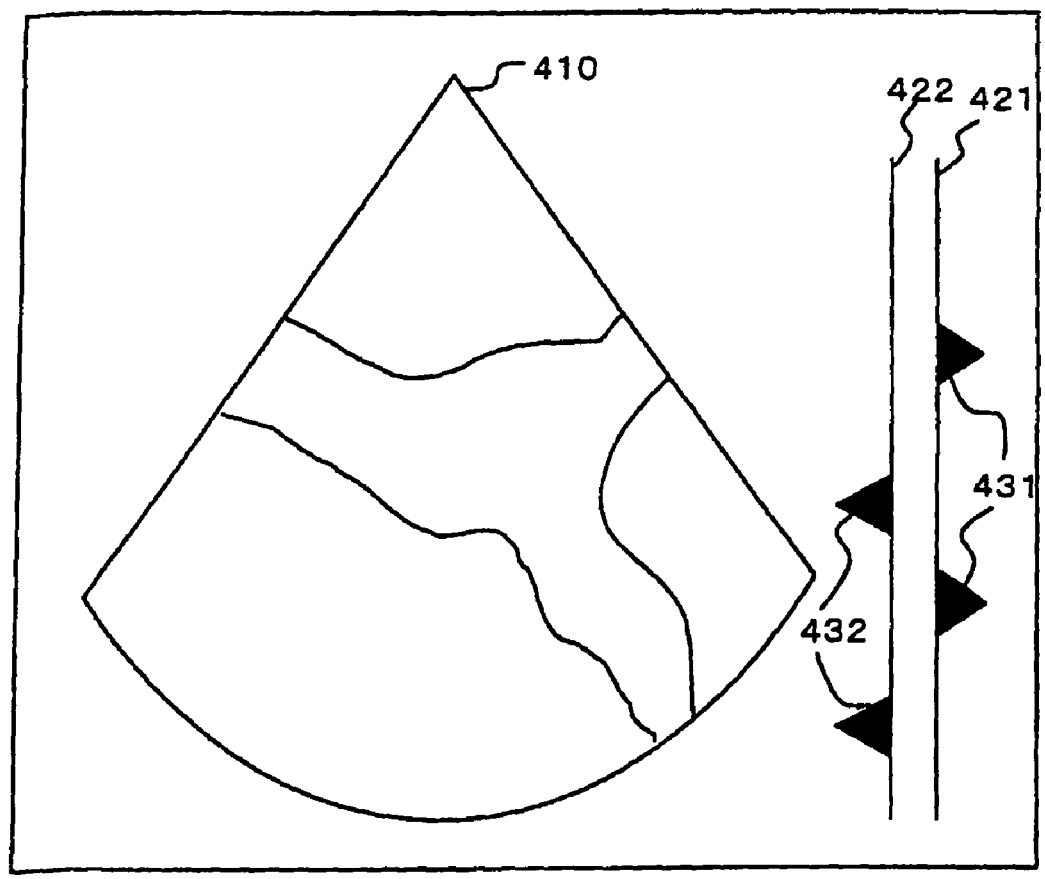
FIG. 4 is a second exemplary illustration of image displayed in a monitor.

As a display mode of the focal points 431 and 432 and the direction line 410, the following modes may be used instead of the display mode shown in FIG. 2. In FIG. 4, direction lines 421 and 422 are displayed, the focal point 431 is located on the direction line 421 which indicates the ultrasonic beam focus in the plane A, and the focal point 432 is located on the direction line 433 which indicates the ultrasonic beam focus in the plane B.

Figure 5:
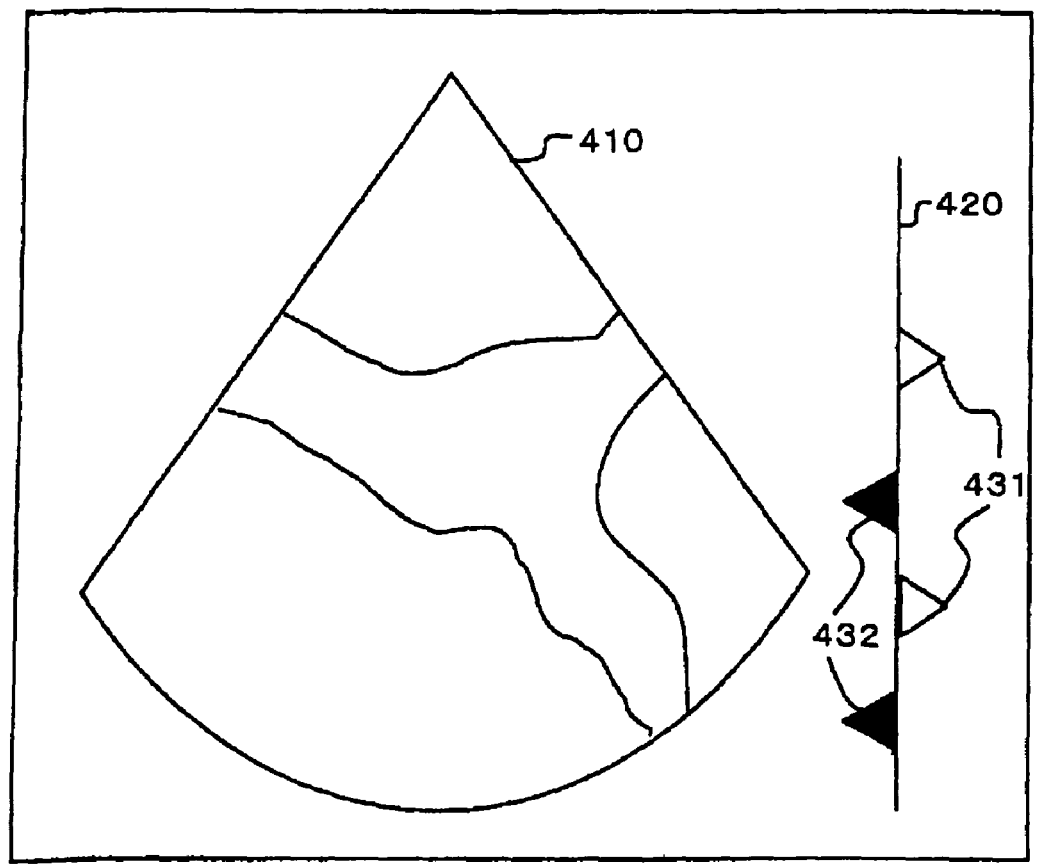
FIG. 5 is a third exemplary illustration of image displayed in a monitor.
Figure 6:
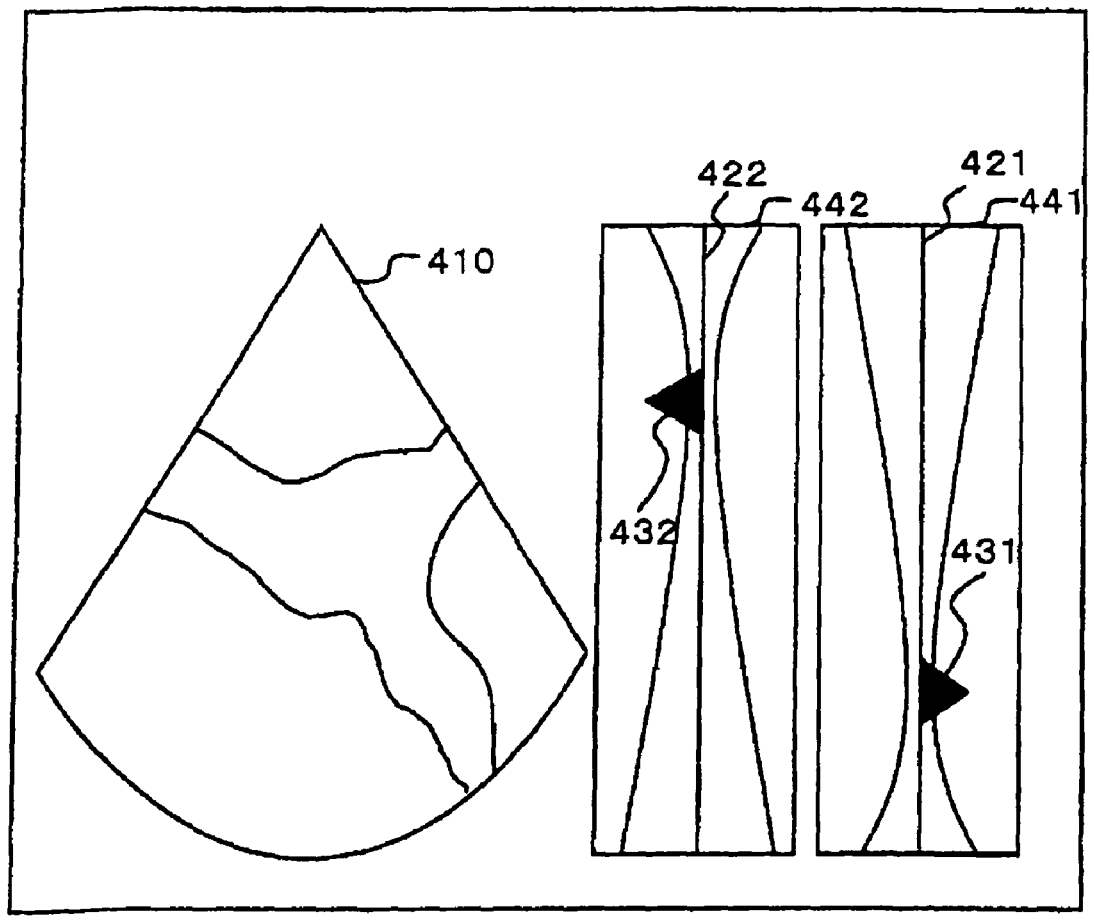
FIG. 6 is a fourth exemplary illustration of image displayed in a monitor.

In FIG. 5, the focal point 431 and the focal point 432 are displayed in different color to be easily discriminated. In FIG. 6, beam form marks 441 and 442 which shows the ultrasonic beam form projected on the planes A and B are displayed.

Figure 7:
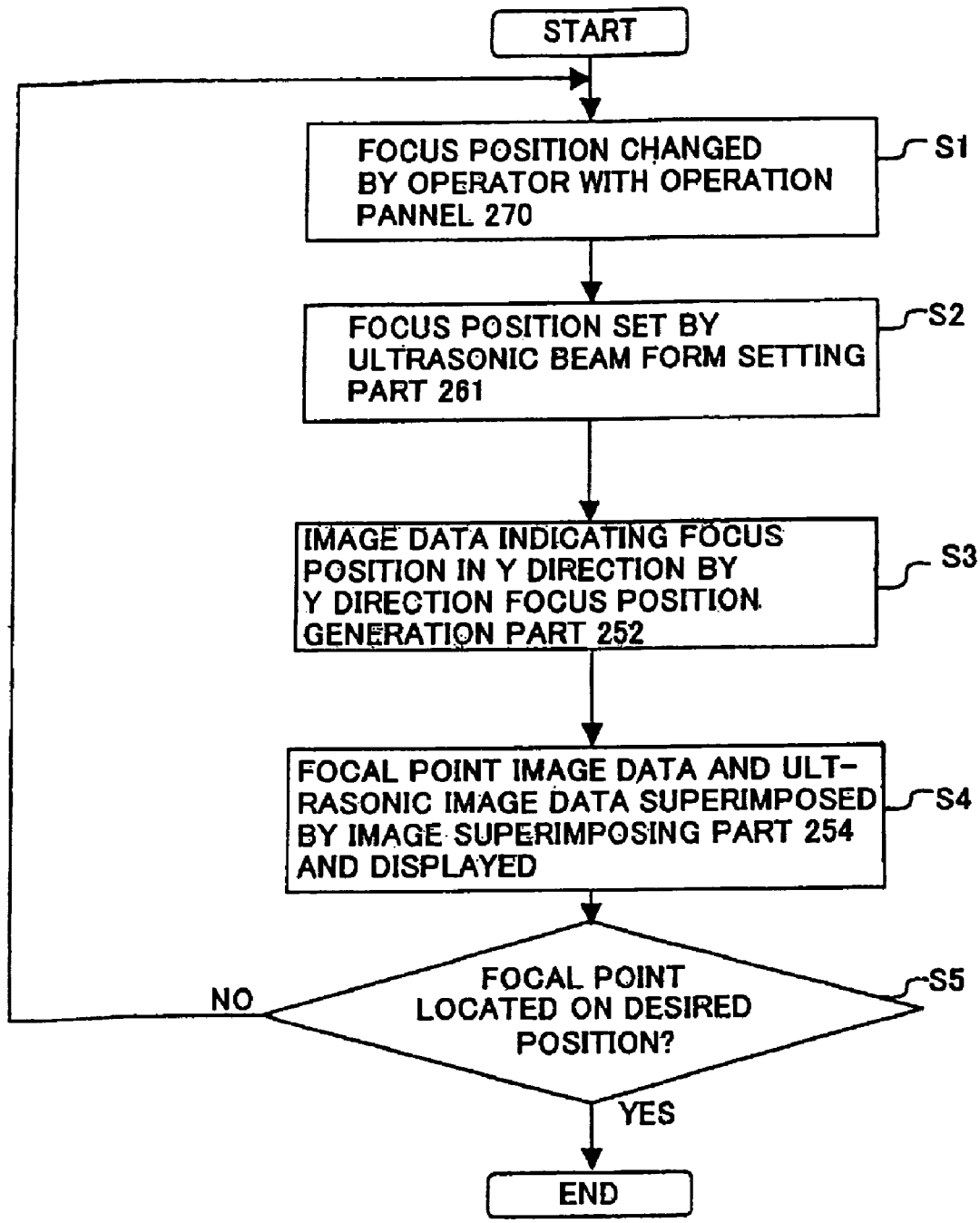
FIG. 7 is a flow chart showing an operation of change of a focus position.

Next, an operation of setting or changing of the focal point is explained with FIG. 7. Although the setting or the changing of the focal point is performed each direction of X and Y, the setting or the changing of the Y directional focal point is mainly explained. The focal point is displayed on the monitor 300 based on the ultrasonic beam form that is set in advance, as shown in FIG. 2, etc. The displayed 2-dimensional sectional image 410 is obtained by scanning the region of interest of the patient OBJ and may be a real time image or a still image that is obtained in advance. Hereinafter, it is explained that the 2-dimensional sectional image 410 is a real-time image.

In Step S1, the operator observes the 2-dimensional sectional image 410 and changes the focus position in the Y direction with the operation panel 270 so that the region of interest is displayed homogeneously. The information related to the amount of change of the focus position is sent from the operation panel 270 to the host CPU 260 when the operator operates the switch, a mouse or the trackball, etc in the operation panel 270.

In Step S2, the ultrasonic beam form setting part 261 in the host CPU 260 sets the ultrasonic beam form based on the information of the amount of change of the focus position. The ultrasonic beam form setting part 261 calculates a relative focus position of the set ultrasonic beam form to the direction line 420 displayed on the monitor 300. The position information of the calculated focal point 432 is transmitted to the Y direction focus position generation part 252. The information of the ultrasonic beam form is sent to the amount calculation part 263 of Y direction delay, and the patient OBJ is scanned on condition of the changed ultrasonic beam form.

In Step S3, the image data of the focal point 432 is created based on the information obtained in Step S2. The image data is sent to the image superimposing part 254.

In Step S4, the image data is superimposed on the 2-dimensional sectional image generated in the ultrasonic image generation part 253, and the superimposed image data is sent to the monitor 300. The focal point 432 according to the change of the focus position is displayed on the monitor 300.

In Step S5, the operator checks whether the focus position is located on a desired position with reference to the image displayed on the monitor 300. In detail, the operator checks positional relationship between the region of interest of the 2-dimensional sectional image 410 and the focal points 431 and 432 and image quality on the region of interest of the 2-dimensional sectional image 410, and determines whether the focus position is appropriate. When the focus position is appropriate, the operator gives a diagnosis or adjusts other parameters. Otherwise, Step S1 is performed again.

Thus, the focal points 431 and 432 is updated when the focus position is changed the ultrasonic image and the beam information on the two planes A and B are displayed in real time.

Figure 8:
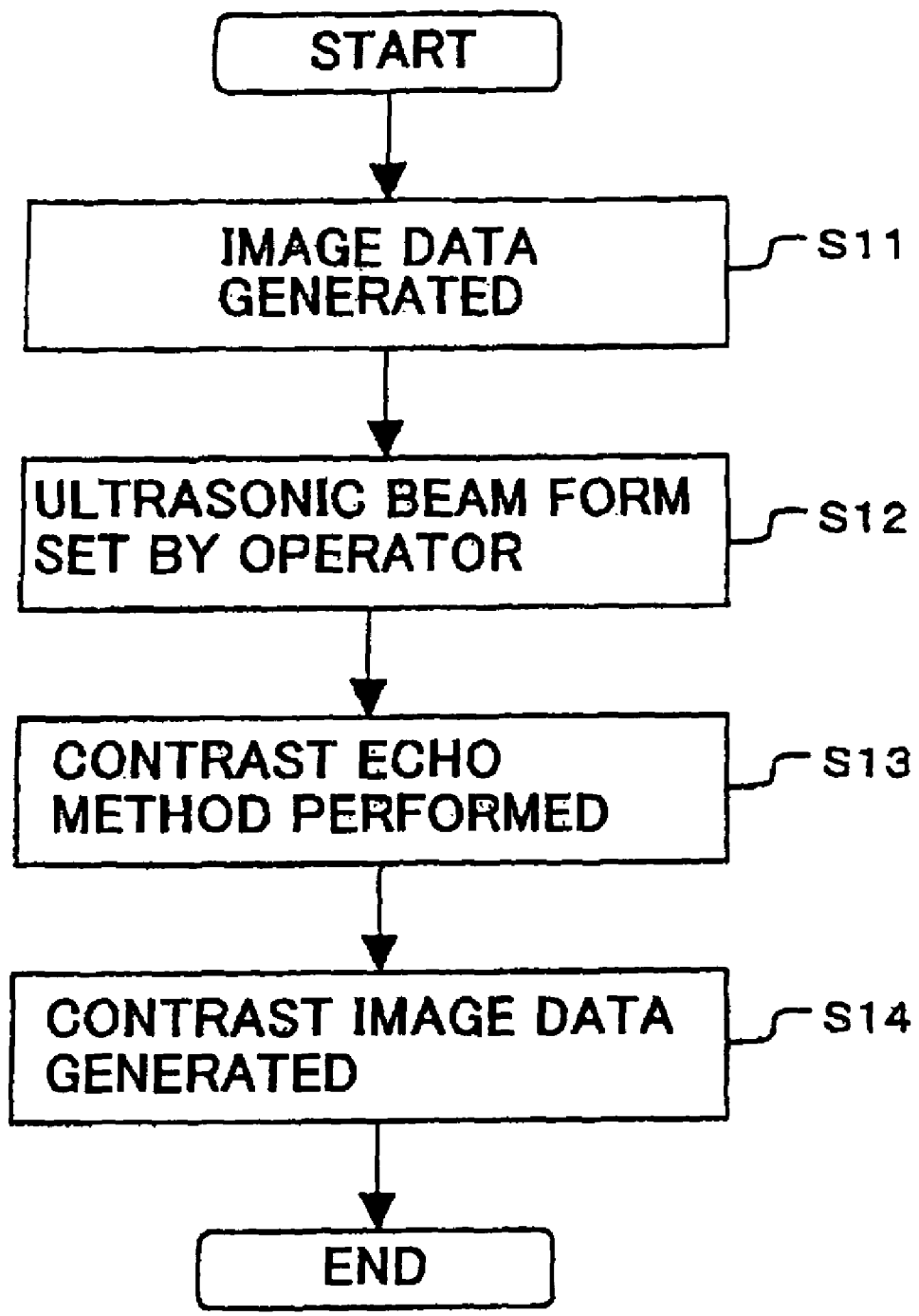
FIG. 8 is a flow chart showing an operation in Contrast Echo method.

Next, an operation of the Contrast Echo method is explained with reference to FIG. 8. In the Contrast Echo method, the contrast agent including the small air bubbles is injected into the patient OBJ, the small air bubbles are destroyed by the ultrasonic wave transmitted from the 2-dimensional array probe, and the harmonic signal generated by the destruction is measured.

In Step S11, the operator instructs scanning of the region of interest in the patient OBJ by the ultrasonic beam transmitted from the 2-dimensional array probe 100. The 2-dimensional sectional image is generated in the main part 200 to be displayed on the monitor 300 as shown in FIG. 2, etc. The focal points 431 and 432 are displayed on predetermined positions based on the beam form that is set in advance.

In Step S12, the operator sets the ultrasonic beam form, referring to the displayed 2-dimensional sectional image 410. The setting is performed by operation of the operation panel 270 to change the focal points 431 and 432. The operator changes the focal points 431 and 432 so that the ultrasonic beam is focused on the region of interest homogeneously.

The operation information is sent to the host CPU 260 from the operation panel 270, the ultrasonic beam form is set, and the amount of delay of the ultrasonic transmission and reception to be given to each ultrasonic transducer is calculated.

In Step S3, the Contrast Echo method is performed. In detail, the ultrasonic beam formed based on memorized amount of delay is transmitted to the region of interest of the patient OBJ homogeneously, the contrast agent is destroyed homogeneously in the region of interest, and the harmonic signal generated by the destruction is measured.

In Step S14, the echo processor 241 generates 3-dimensional contrast image data based on the obtained harmonic signal. The generated 3-dimensional contrast image data is sent to the display processing part 250, the display processing part 250 generates a plurality of sets of 2-dimensional sectional image data on a predetermined section, sectional images are displayed on the monitor 300 with or without a 3-dimensional contrast image.

When a position of the biopsy needle during being inserted into to the patient OBJ is confirmed or when continuity of a blood vessel is confirmed using the Color Flow Mapping method in which a B-mode sectional image is superimposed on color blood vessel image, the focal position is adjusted since the homogeneity of image is required. In this case, an operation of the ultrasound imaging apparatus is the same as or similar to the operation shown in FIG. 8. Referring to the 2-dimensional sectional image of the patient OBJ, the operator adjusts the focus position so that a region from a surface of the patient to a portion which the biopsy needle is injected to is displayed homogeneously.

Figure 9:
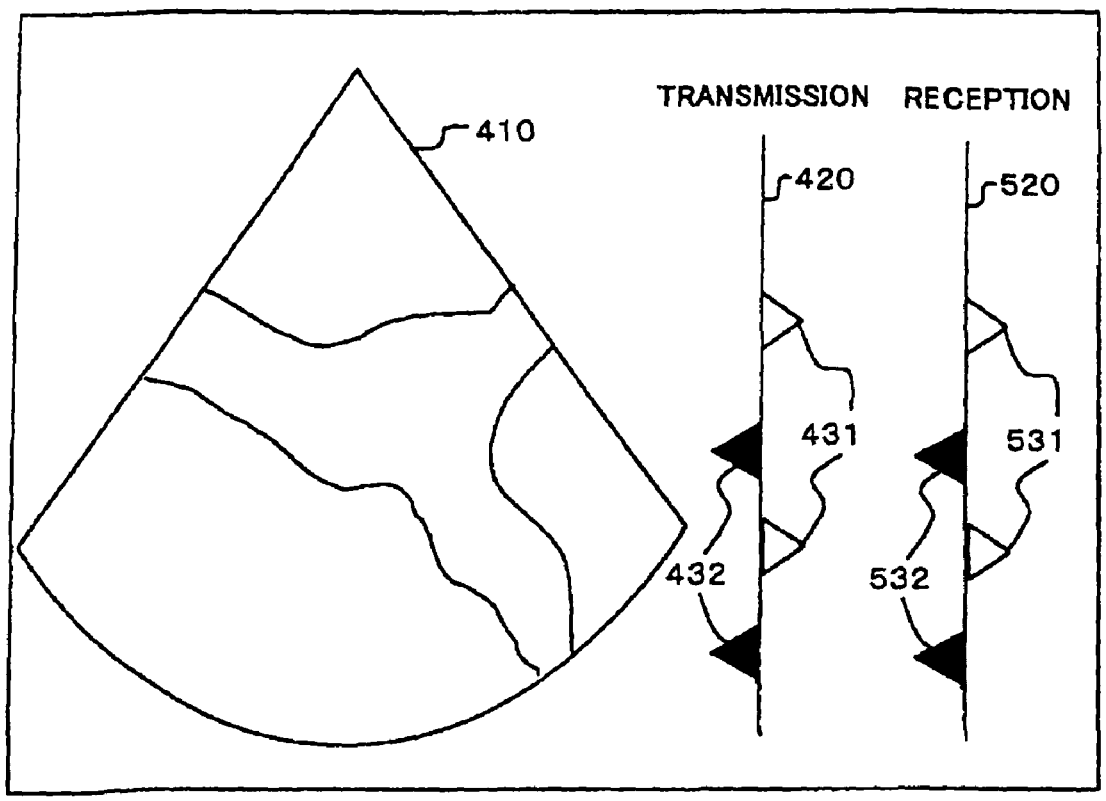
FIG. 9 is a modified exemplary illustration of image displayed in a monitor.

Next, a modification of the embodiment is explained with reference to FIG. 9. Although it is explained that only transmitted ultrasonic beam form is set, as an example, in the above embodiment, a focus point in reception can be also set with the operation panel 270 in the modification. In this case, as shown in FIG. 9, the focus position in transmission and the focus position in reception are displayed in different mode according to number of transmission and reception. In detail, as well as transmission, the focal points of reception in X and Y directions are displayed on a direction line 520 in different mode. The operator confirms and sets the ultrasonic beam form in reception with reference to the focal points 531 and 532.

Although it is explained the 2-dimensional array probe is used in the above embodiment or modification, another ultrasound imaging apparatus which can set the focal points in at least two different planes respectively may be used. For example, a 1.5 D array probe which also controls the focus positions in two directions may be used.

As explained above, according to the embodiment and modification, the ultrasound imaging apparatus in which the focus positions in at least two directions is easily recognized and set can be provided.

Moreover, when the focal points in two directions are displayed with the 2-dimensional sectional image, the operator can recognize the ultrasonic beam form more easily. The operator can easily recognize the positional relationship between the region of interest and the ultrasonic beam form by referring to the simultaneously displayed 2-dimensional sectional image.

Furthermore, since the ultrasonic beam form is set or changed by moving the two focal points, referring to the 2-dimensional sectional image, the setting of the ultrasonic beam forms in the two directions is easily performed.

Since the focal points can be set in two directions, the ultrasonic beam form whose focus is homogeneous in a wide region can be set when the focus positions are different in the plane A and plane B as shown in FIG. 3. In the conventional multi-focus method, the frame rate or the image quality of defocus of the ultrasonic beam is reduced, however in the ultrasonic imaging apparatus in the embodiment or modification, a high frame rate or a high quality of image in a wide region can be achieved.

The homogeneous image of high quality in a wide range is very useful, especially in the Contrast Echo method or in the Color Flow Mapping or the biopsy needle insertion method. Therefore, according to the embodiment or modification, it is easy to find or treat a diseased region.

The present invention may not be limited to the above embodiment or modification, and may also include other modifications. For example, although it is explained that the focus positions in two directions are displayed simultaneously in the above embodiment and modification, the focus positions may be displayed alternatively under control of an additional selecting part. Further, it may be selected with the selecting part whether the focus position is displayed or not. Moreover, although it is explained that the 2-dimensional array probe is used in the above embodiment and the modification, an 1-dimensional array probe which can move the focus points in two directions electrically and mechanically may be used.

What is claimed is:

1. An ultrasound imaging apparatus, comprising:
   a two-dimensional ultrasonic probe configured to transmit an ultrasonic beam a number of times to an object and receive a reflective ultrasonic signal based on each transmission;
   a controller configured to control the ultrasonic probe such that the ultrasonic beam is focused on a first variable focus position in a first direction and a second variable focus position in a second direction independently of each other, the first direction and the second direction are substantially perpendicular to a transmitting and reception direction and each other;
   an image generation unit configured to generate an ultrasonic image based on the number of reflective ultrasonic signals; and
   a display unit configured to display a number of focus positions corresponding to the number of transmissions and receptions in the first and second directions with the ultrasonic image.

2. The ultrasound imaging apparatus according to claim 1, wherein the ultrasonic probe includes a plurality of ultrasonic transducers arranged in two directions.

3. The ultrasound imaging apparatus according to claim 2, wherein the controller controls delay time in transmission and reception of the ultrasonic beam in the two directions of arrangement of the ultrasonic transducers.

4. The ultrasound imaging apparatus according to claim 2, wherein the ultrasonic transducers are arranged in the two arrangement directions corresponding to the two directions of the focus positions.

5. The ultrasound imaging apparatus according to claim 2, wherein the plurality of ultrasonic transducers is at least five in each direction.

6. The ultrasound imaging apparatus according to claim 1, wherein the display unit displays the focus positions in at least one of different positions, different colors and different shapes in response to the first and second directions.

7. The ultrasound imaging apparatus according to claim 1, wherein the display unit displays a transmission beam form of the ultrasonic beam.

8. The ultrasound imaging apparatus according to claim 1, including an input unit configured to input the first variable focus position and the second variable focus position.

9. A method of ultrasound imaging, comprising:
   transmitting an ultrasonic beam a number of times in at least two directions to an object by a two-dimensional ultrasonic probe;
   receiving a reflective ultrasonic signal based on each transmission;
   controlling the ultrasonic probe such that the ultrasonic beam is focused on a first variable focus position in a first direction and a second variable focus position in a second direction independently of each other, the first direction and the second direction are substantially perpendicular to a transmitting and reception direction and each other;
   generating an ultrasonic image based on the number of reflective ultrasonic signals; and
   displaying a number of focus positions corresponding to the number of transmissions and receptions in the first and second directions with the ultrasonic image.

10. The method of ultrasound imaging according to claim 9, wherein the displaying includes displaying the focus positions in at least one of different positions, different colors and different shapes in response to the first and second directions.

11. The method of ultrasound imaging according to claim 9, wherein the displaying includes displaying a transmission beam form of the ultrasonic beam.

* * * * *